(12) United States Patent
Plank et al.

(10) Patent No.: US 8,142,188 B2
(45) Date of Patent: Mar. 27, 2012

(54) LIGHT CURING DEVICE/BASE STATION COMBINATION

(75) Inventors: Wolfgang Plank, Rankweil (AT); Bruno Senn, Buchs (CH)

(73) Assignee: Ivoclar Vivadent A.G., Schaan (LI)

( * ) Notice: Subject to any disclaimer, the term of this patent is extended or adjusted under 35 U.S.C. 154(b) by 99 days.

(21) Appl. No.: 12/079,069

(22) Filed: Mar. 24, 2008

(65) Prior Publication Data

US 2008/0233534 A1  Sep. 25, 2008

Related U.S. Application Data

(60) Provisional application No. 60/931,578, filed on May 24, 2007.

(30) Foreign Application Priority Data

Mar. 22, 2007 (DE) .......................... 10 2007 013 783

(51) Int. Cl.
*A61C 1/00* (2006.01)

(52) U.S. Cl. ........................................ 433/29; 433/141

(58) Field of Classification Search ............... 433/29, 433/32, 35, 49–50, 77, 141; 362/580, 573, 362/294, 373; 606/2–19
See application file for complete search history.

(56) References Cited

U.S. PATENT DOCUMENTS

| | | | |
|---|---|---|---|
| 4,308,012 A * | 12/1981 | Tamler et al. | 433/32 |
| 5,271,087 A | 12/1993 | Schmid | |
| 5,382,162 A * | 1/1995 | Sharp | 433/116 |
| 5,997,297 A * | 12/1999 | Coburn et al. | 433/77 |
| 6,709,128 B2 * | 3/2004 | Gordon et al. | 362/119 |
| 6,991,356 B2 | 1/2006 | Tsimerman | |
| 7,144,250 B2 * | 12/2006 | Fischer et al. | 433/29 |
| 7,195,482 B2 * | 3/2007 | Scott | 433/29 |
| 2002/0168607 A1 * | 11/2002 | Cao | 433/29 |
| 2003/0032950 A1 * | 2/2003 | Altshuler et al. | 606/9 |
| 2003/0152885 A1 | 8/2003 | Dinh | |
| 2006/0024638 A1 * | 2/2006 | Rosenblood et al. | 433/29 |
| 2006/0040231 A1 | 2/2006 | Quan | |
| 2006/0285328 A1 * | 12/2006 | Syribeys | 362/257 |

OTHER PUBLICATIONS

U.S. Appl. No. 60/292,827 cited in paragraph [0168] of US provisional application 2003/0032950 published Feb. 13, 2003.

* cited by examiner

*Primary Examiner* — Cris L Rodriguez
*Assistant Examiner* — Edward Moran
(74) *Attorney, Agent, or Firm* — John C. Thompson; Sandra J. Thompson

(57) ABSTRACT

The invention relates to a light curing device/base station combination, comprising a heat absorbing element, which is in particular metallic, and which is in thermally conducting connection with a heat source, in particular a light source, and in particular comprising a handle. The base station (12) has for the light curing device (14) a heat dissipating device(27), which lies against the heat absorbing element (24) when the light curing device (14) is accommodated in or on the base station (12).

14 Claims, 5 Drawing Sheets

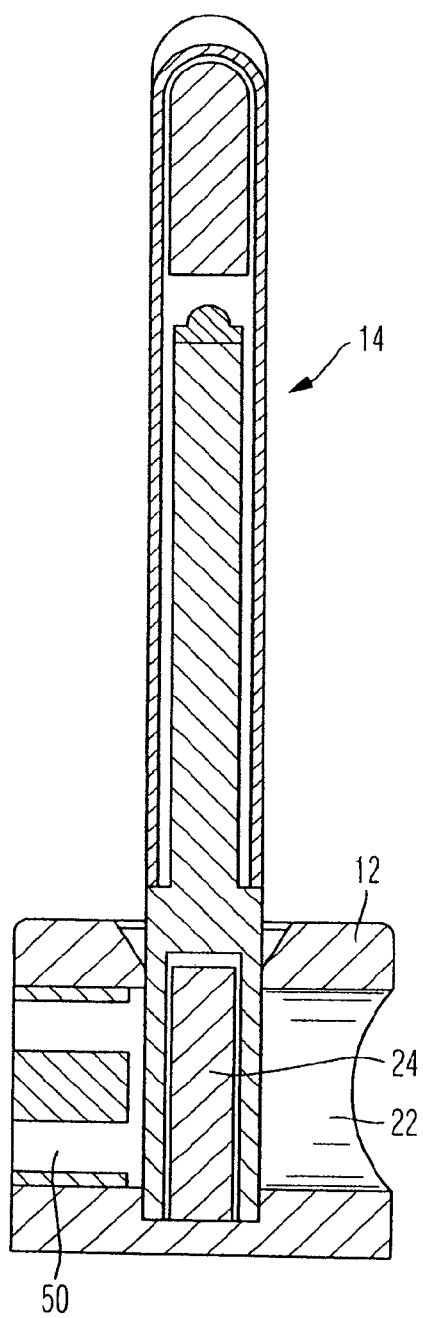
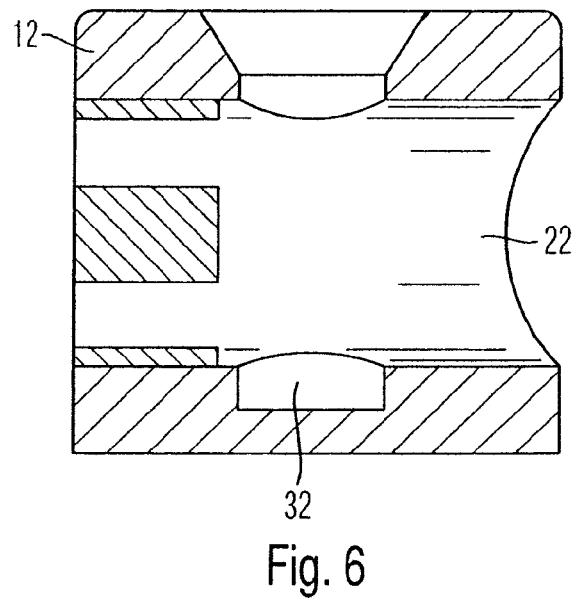
Fig. 6
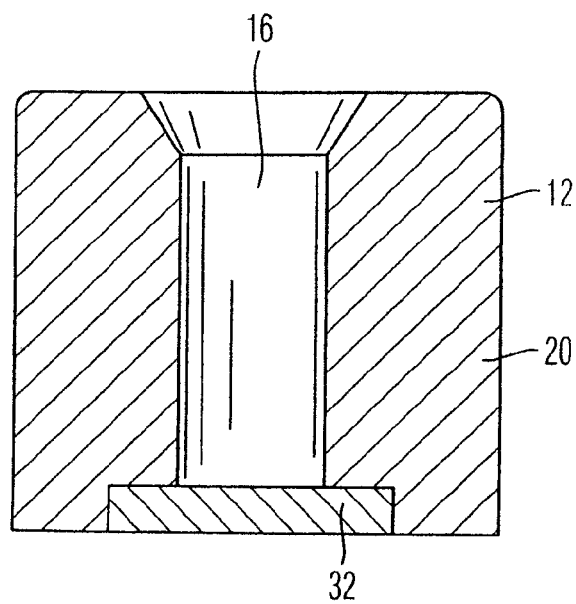
Fig. 7
Fig. 5

LIGHT CURING DEVICE/BASE STATION COMBINATION

CROSS-REFERENCE TO RELATED APPLICATIONS

This application claims foreign priority benefits under 35 U.S.C. §119(a)-(d) from German patent application ser. no. P 10 2007 013 783.6 filed Mar. 22, 2007. In addition, this application claims the benefit under 35 U.S.C. §119(e) of U.S. provisional patent application Ser. No. 60/931,578 filed May 24, 2007.

TECHNICAL FIELD

The invention relates to a light curing device/base station combination, and more particularly to a light curing device/base station combination comprising a heat absorbing element, which is in particular metallic, and which is in thermally conducting connection with a heat source, in particular a light source, and in particular comprising a handle.

BACKGROUND OF THE INVENTION

Such a light curing device is known for example from DE-A1-41 24 412. In the case of this solution, a light curing device of a stick-like form has a heat exchanger, which is formed at the rear end of the light curing device. A heat exchange is intended to be ensured by an appropriate heat exchange element and a supply line.

Furthermore, it is known per se to use a relatively solid body in a light curing device as the thermal capacitance and accordingly to use it as a heat sink for LEDs used as light sources.

The provision of compact thermal capacitances in the light curing device has the advantage that there is no need for the latter to include a fan, which is susceptible to faults but also prevents the light curing device from being sterilizable, since sterilizing fluid can constantly get into the housing openings required for the fan.

However, such solutions have not so far been very successful commercially, since they cause a considerable cycle time, on account of the cooling phase required for the cooling of the thermal capacitance. Especially in the case of light sources with a high output, that is to say using LEDs with a luminous flux of over 100 lumen, such solutions are therefore not practicable.

OBJECTS AND SUMMARY OF THE INVENTION

An object of the present invention is to provide a light curing device/base station combination which is suitable for the use of at least one LED with a high light output or a high luminous flux, but nevertheless permits an acceptable cycle time, and is nevertheless sterilizable.

According to the invention, it is particularly favorable that the housing of the light curing device can be smooth on the outside, take the form of a stick and to this extent be compact.

According to the invention, the rear region is formed as a heat exchange region, and it is precisely there that the increased thermal capacitance is provided for fan-free cooling of the light source.

By insertion in a base station, rapid cooling of the heat store can be achieved on account of the comparatively large heat transfer area with low thermal resistance, which for the first time permits a correspondingly short cycle time for such sterilizable light curing devices.

According to the invention, it is particularly favorable that rapid heat dissipation can take place as a result of the intensive contact between the heat absorbing element of the base station and the cooling device. For this purpose, the cooling device of the base station may have a thermal capacitance of its own, which may well be higher by a factor of 10 for example than the thermal capacitance of the heat absorbing element in the light curing device. As a result, rapid heat dissipation is ensured, it being possible in turn for the thermal capacitance of the cooling device to be cooled in any desired suitable way, for example by a fan, so that it is readily at room temperature again for the next cycle, and so has an intensive cooling effect This provides the possibility of using a comparatively small and accordingly lightweight thermal capacitance of the heat absorbing element of the light curing device nevertheless to achieve a rapid cycle time along with an ergonomically favorable configuration of the light curing device. It is preferred in this connection that the actual heat absorbing element is metallic, for example made of copper, including its surface. To protect the user's hand, a sliding sleeve, which automatically covers the heat absorbing element, consists for example of plastic and covers the heat absorbing element in a spring-loaded manner when the light curing device is not in the base station, may be provided here.

For the fitting of the light curing device into the base station, the light curing device can be quite simply inserted with its rear end into a corresponding recess in the base station. As a result, the sliding sleeve, which may be provided according to an advantageous configuration, is pushed back.

The recess in the base station is dimensioned with preference in such a way that the light curing device enters the recess over the entire region of its heat absorbing element and a heat transfer area of a large surface area is available.

According to the invention, it is particularly favorable that the light curing device can be extremely slender and stick-like. This makes handling much easier, and it is also much more possible to perform the curing of distal sides of molars, in particular if the tip of the light curing device is bent away with the light exiting end, so that lateral light emission is made much easier.

According to the invention, it is particularly favorable that the light source may be either adjacent the heat absorbing element, that is to say to this extent as it were automatically in intensive thermally conducting connection with the latter, or formed on the front end of the light curing device. In the first case, a light guide is provided, extending through much more than half the housing of the light curing device and also deflecting the light emission to the lateral light exiting area. In the second case, the light source may be arranged either shortly before the deflection of the light emission, or even just after the light exiting area. In both cases, a heat conductor then extends between the light source and the heat absorbing element, the housing that surrounds the heat conductor being formed with preference from a heat-insulating material, such as plastic.

In an advantageous configuration, it is provided that the rear side of the light curing device, that is to say the rear end face, is formed either directly by the heat absorbing element or by means of a metallic terminating area, which is in thermally conducting connection with the heat absorbing element. This area can be used particularly well for the heat transfer from the heat absorbing element to the cooling device of the base station.

It is also possible to provide a cooling element such as a Peltier element at this location in the base station, that is to say at the bottom of the recess in the form of a blind hole in the base station for receiving the light curing device, the temperature of which element lowered to a temperature well below room temperature, by applying a current, when the cooling of the light curing device is to be performed. This allows its heat transfer to be speeded up further, so that, after it is inserted into the base station, the heat absorbing element reaches room temperature already after quite a short time, for example 10 seconds.

Here it is also possible to pre-cool the heat absorbing element as it were before switching on the light source, in order then to have a greater heat absorbing capacity available.

The embodiment with the light source adjacent the light exiting end has quite a solid heat conductor. Its thermal capacitance can be used in addition to the thermal capacitance of the heat absorbing element for storing heat or cold.

However, this makes the light curing device somewhat heavier, so that the version with the light source in the direct vicinity of the heat absorbing element is preferred when light-weight light curing devices are the objective.

According to a further particularly preferred configuration, it is envisaged to configure the housing of the light curing device such that it surrounds the light source and is reflective in front of the light source. A coating applied to the inside of the plastic housing of the light curing device is provided with preference for this purpose. It is particularly preferred in this connection if a single light-emitting diode in the form of a corresponding LED chip is applied and the diameter of the light curing device is chosen to be extremely thin, so that handling in the manner of a pencil is possible. The diameter of the light curing device may be, for example, 8 millimeters, or else 12 millimeters, so that the light source can be accommodated centrally in the light curing device. Given a wall thickness of the housing of the light curing device of I millimeter, an air gap of, for example, 1 millimeter can still be left, serving for heat insulation, so that the light source does not come into contact directly with the housing of the light curing device consisting of plastic.

It is also possible to activate cooling automatically by inserting the light curing device into the base station. For this purpose, a fan may be switched on for example, with preference providing a lateral air stream through the base station and passing it along cooling ribs which cool the heat store of the base station. In addition or as an alternative, a cooling element, such as for example a Peltier element, can be switched on by this action.

In a further advantageous configuration, it is provided that a heat transfer area with a thermal resistance of less than 10 W/° K, in particular less than 2 W/° K, can be accommodated in the base station.

In a further advantageous configuration, it is provided that the housing of the hand piece itself or a heat store of the hand piece forms a heat exchange area which lies against the base station.

In a further advantageous configuration, it is provided that the heat absorbing element has a thermal capacitance which corresponds to the thermal capacitance of a copper element of approximately 0.5 to 30 cm$^3$, in particular 2 cm$^3$, and is arranged in particular in the rear region of the light curing device. In an alternative configuration, it is envisaged to concentrate the arrangement of the thermal capacitance of the heat absorbing element on the central region of the light curing device, so that the rear region thereof can be formed to some extent such that it is thermally separate from a handle.

In a further advantageous configuration, it is provided that in front of the light source there extends a light guide, which is bent away at the end, in particular by an angle of between 10° and 130°, with preference approximately at right angles.

In a further advantageous configuration, it is provided that a bent-away portion is 10 provided at the front end of the light guide, extending laterally by less than the diameter of the light curing device.

In a further advantageous configuration, it is provided that the light curing device is substantially in the form of a stick and has a length/diameter ratio of more than 5 to 1, in particular approximately 12 to 1.

In a further advantageous configuration, it is provided that the light curing device, in particular of a stick-like form, can be received in a recess in the base station.

In a further advantageous configuration, it is provided that the heat absorbing element is arranged between the front end region, on the light exiting side, and the handle and/or in the region of the handle.

In a further advantageous configuration, it is provided that the heat absorbing element lies against the base station directly, via the housing or via a heat exchange element.

In a further advantageous configuration, it is provided that at least part of the heat dissipating device is formed by a heat store.

In a further advantageous configuration, it is provided that the heat store can be brought into thermally conducting connection with the heat absorbing element.

In a further advantageous configuration, it is provided that the heat absorbing element and a receiving region of the base station that is in connection with the heat store have cross sections interacting in a positively engaging manner.

In a further advantageous configuration, it is provided that the light curing device located in the base station receptacle is at least partially in contact with the base station directly.

In a further advantageous configuration, it is provided that the rear end region of the light curing device and/or the opening of the receiving region at the upper end of the recess in the base station has a flared insertion portion.

In a further advantageous configuration, it is provided that the thermal capacitance of the heat store is at least twice, in particular approximately 5 times, the thermal capacitance of the heat absorbing element.

In a further advantageous configuration, it is provided that the base station has a fan and/or cooling ribs and that a cooling air stream passes through the base station transversely in relation to the extent of the light curing device that is accommodated in the base station.

In a further advantageous configuration, it is provided that the base station has a cooling element, for example a Peltier element, which is in thermally conducting connection with the light curing device when it is in the state of being inserted in the base station.

In a further advantageous configuration, it is provided that the light curing device bears a sliding sleeve, which covers the heat absorbing element at the rear end region of the light curing device, in particular in a spring-loaded manner, when the light curing device is not inserted in the base station.

In a further advantageous configuration, it is provided that the light curing device is held in the base station by magnetic force.

In a further advantageous configuration, it is provided that there is a highly heat-conducting gel in the receiving region of the base station.

In a further advantageous configuration, it is provided that at least part of the heat dissipating device in the base station is formed by a heat pipe.

Further advantages, details and features of two embodiments are provided by the following description of the invention on the basis of the drawing, in which:

BRIEF DESCRIPTION OF THE FIGURES

FIG. 5 shows a sectional representation of a light curing device that is fitted in a base station, in an embodiment of the light curing device according to the invention;

FIG. 6 shows a sectional representation of the base station as shown in FIG. 5;

FIG. 7 shows a sectional representation of the embodiment of the base station as shown in FIG. 6, but from a different direction;

DETAILED DESCRIPTION

Figure 1:
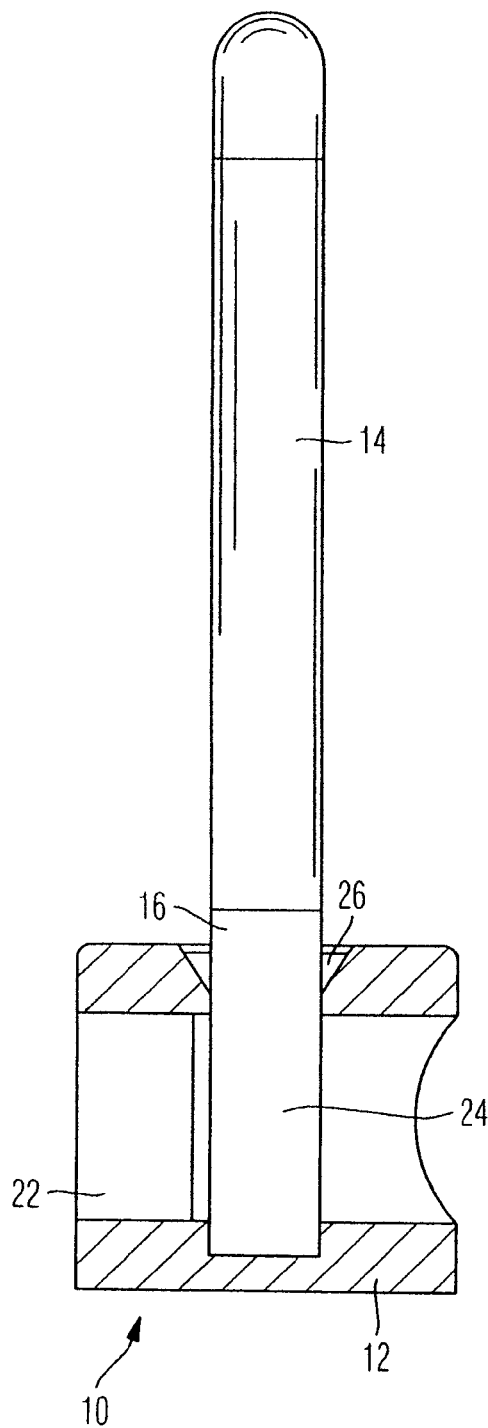
FIG. 1 shows a schematic representation of an embodiment of a light curing device according to the invention.

The combination 10, schematically represented in FIG. 1, of a light curing device 14 and a base station 12 is distinguished in this embodiment by the fact that the light curing device 14 is of a substantially stick-like form. In this embodiment, the stick-like light curing device 12 is inserted in a receptacle 16, which is provided in the base station 12 and forms a receiving region for the light curing device.

Instead of that, the light curing device may also have any other desired form, for example also the form of a pistol, a rear or central region then at least being brought into contact with the base station.

In the exemplary embodiment represented in FIG. 1, the base station 12 is formed as a quite compact body, substantially in the form of a cube or a virtually cuboidal cylinder. The base station 12 substantially comprises parts of metal, such as for example copper, so that it forms a heat store 20. In addition, it has a transversely extending flow channel 22, which accommodates a small fan, and directs an air flow with a cooling effect through the base station. As a result, the light curing device 14 is at the same time cooled in its rear region, which has a heat absorbing element 24.

The heat store 20, and possibly the additionally provided flow channel 22 with the cooling effect thus provided, to this extent forms a heat dissipating device 27.

In the exemplary embodiment represented, the base station 12 is quite compact and has, for example, approximately three times the diameter of the light curing device 14. In an alternative configuration, however, it is much larger and has a heat store 20, the thermal capacitance of which is greater by a power of ten than the thermal capacitance of the heat absorbing element 24.

Provided on the recess 16, in the upper region, is a flared insertion portion 26, which facilitates the insertion of the light curing device 14.

The relative dimensions of the recess 16 on the one hand and of the light curing device 14 on the other hand are chosen such that a play-free fit is ensured. As a result, the heat absorbing element 24 lies flush and over a large surface area in the recess 16, so that a good heat transfer is ensured.

The light curing device 14 is of a substantially stick-like form and has in its rear region the heat absorbing element 24 with a metallic outer surface. The metallic outer surface is arranged as a heat exchange element 25 with the actual absorbing element. By contrast, the housing of the light curing device 14 is otherwise made of plastic, so that to this extent heat insulation is obtained.

In the exemplary embodiment represented, the length of the light curing device 14 is chosen such that the dentist can readily grasp the light curing device 14 in the region of the plastic housing 30 and perform the desired handling. Alternatively, it is also possible to provide a sliding sleeve—if need be a removable sliding sleeve—which, when the light curing device 14 is taken out from the recess 16, automatically moves to the rear into the region of the heat absorbing element 24 and, as it were, protects the latter from contact.

Figure 2:
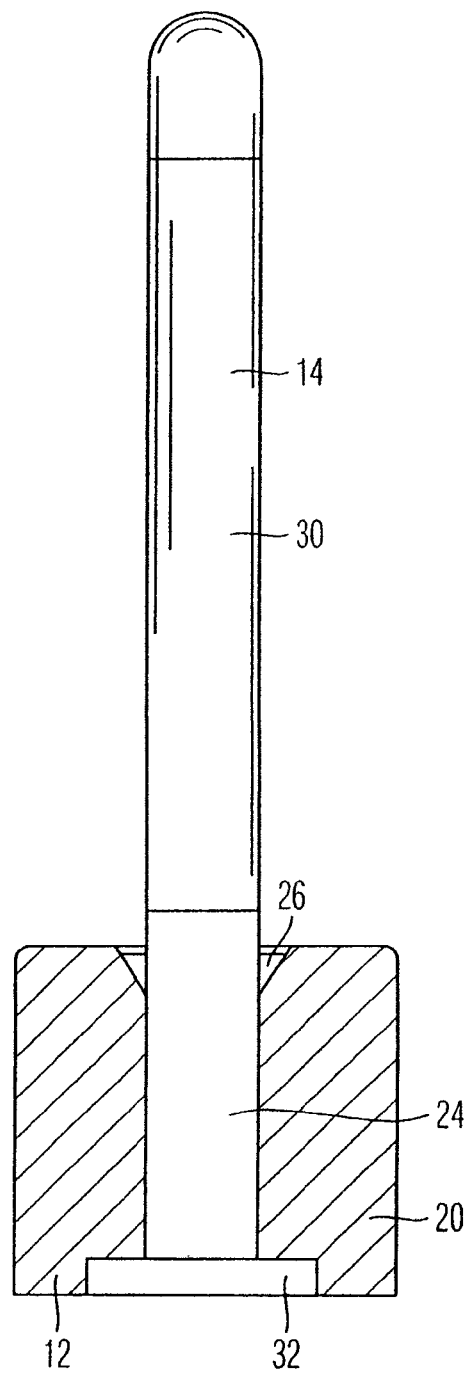
FIG. 2 shows a representation of a further embodiment of the light curing device according to the invention as shown in FIG. 1.

A modified configuration of the light curing device according to the invention can be seen in FIG. 2. Provided there instead of the forced ventilation with a fan, as schematically indicated in FIG. 1, is a Peltier element 32, which has a cooling effect and is likewise in intensive thermal contact with the heat absorbing element 24 when the light curing device 14 is fitted in the recess 16. In the case of this solution, the Peltier element 32 directly cools the heat absorbing element 24 from its end face. In addition, the heat store 20 is cooled and, indirectly via the heat store 20, the heat absorbing element 24 is also cooled from the side.

It is self-evident that, if need be, the two embodiments with the fan and the cooling element can also be combined.

Figure 3:
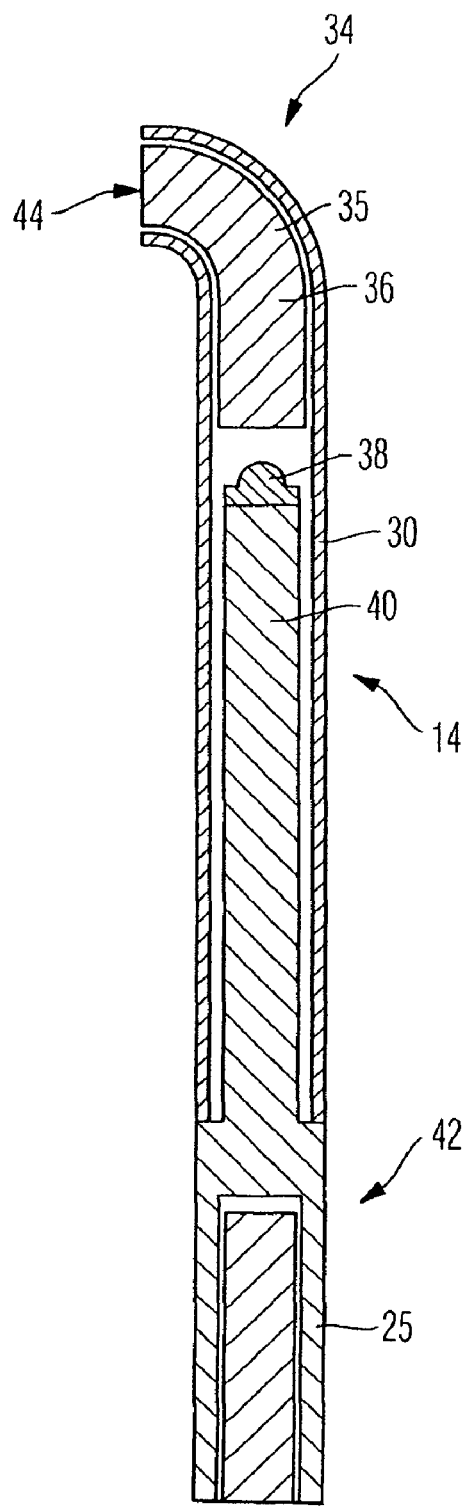
FIG. 3 shows a sectional representation of an embodiment of the hand piece for a light curing device according to the invention.

A light curing device 14 can be seen in section in FIG. 3. The light curing device 14 has the plastic housing 30, which extends over a large part of the stick-like light curing device 14. The light curing device 14 is bent away to the side in a front region 35, with a bent-away portion 34. A light guide 36, which is formed by an LED chip, is provided in front of a light source 38. The LED chip is mounted on a heat conductor 40, which extends quite far forward, that is to say in the exemplary embodiment represented as far as the front quarter of the light curing device 14. The heat conductor 40 and the light source 38 are laterally away from the plastic housing 30, for example by 0.5 to 2 millimeters, so that to this extent heat insulation is additionally obtained.

In the exemplary embodiment represented, the heat conductor 40 is formed in its rear region 42 as a sleeve and accommodates the heat absorbing element 24. The heat absorbing element 24 is formed from a metal with a particularly high thermal capacitance, while the heat conductor 40 consists with preference of aluminum or some other lightweight metal.

As an alternative to the heat exchange element 24, which fills the rear region of the light curing device as a kind of core, the rear region may also be solidly formed, that is to say the heat exchange element 24 forms the rear region itself. With preference, in this embodiment the heat exchange element 24 is of the same material as the heat conductor 40.

The light guide 36 ends at a light exiting area 44, which extends laterally, that is to say at an angle of 90°, in relation to the light exiting direction of the light source 38. In order to ensure a light yield that is as high as possible, the housing 30 is reflectively coated on the inside. The light radiation emitted by the light source 38 is consequently also reflected laterally and directed to the light guide 36—possibly with the assistance of optical means such as reflectors or lenses, so that good light efficiency is ensured.

Figure 4:
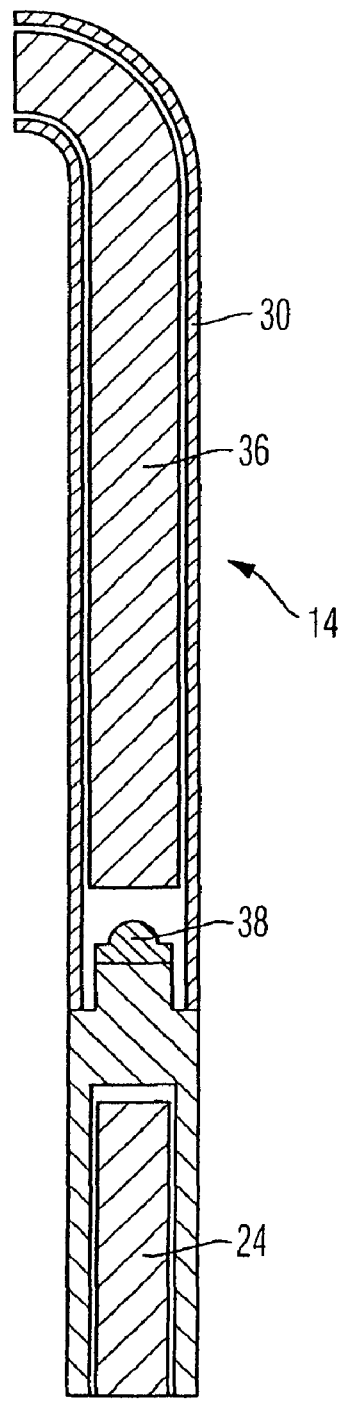
FIG. 4 shows a sectional representation of a further embodiment of a light curing device according to the invention.

It can be seen from FIG. 4 in what way the light source 38 can be alternatively arranged. There, the heat conductor 40 is made much shorter and extends over a very short region, such as for example over a length which corresponds to the diameter of the light curing device 14. The light source 38 is therefore closely adjacent the heat absorbing element 24.

Here, too, the light exiting takes place through a light guide 36, which is made much longer and extends for example over ⅔ of the stick-like light curing device.

It can be seen from FIG. 5 in what way the light curing device 14 inserted in the base station 12 can be cooled. Here, in a way corresponding to FIG. 1, a cooling air stream is provided in the flow channel 22, a fan 50 being schematically represented in FIG. 5.

FIG. 6 shows an enlarged representation of the flow channel 22 from FIG. 5, but without a fitted light curing device 14. It is evident that, in the case of this solution, the heat absorbing element 24 is intensively exposed to the air stream of the flow channel 22, while the rearmost end of the heat absorbing element 24 is inserted in a short blind-hole bore 52 of the base station 12. An intensive heat transfer likewise takes place there, assisting the cooling.

It can be seen from FIG. 7 how the base station 12 may be configured as an alternative. Here it is evident that the heat store 20 is made much larger, as a solid copper block. Cooling of the light curing device 14, when it is inserted, takes place by means of the Peltier element 32 there.

Figure 8:
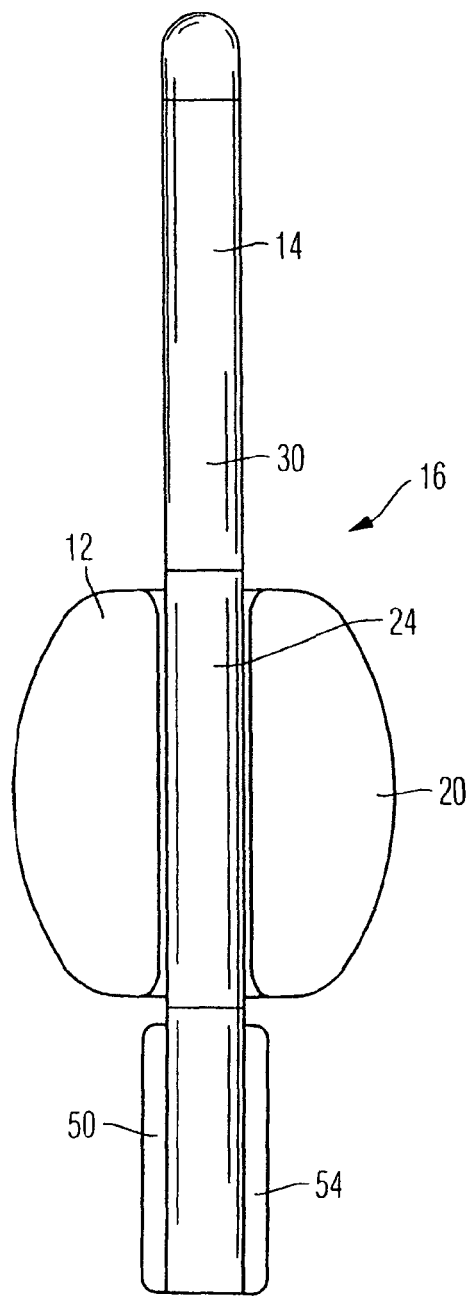
FIG. 8 shows a further embodiment of a light curing device according to the invention.

FIG. 8 shows a modified configuration of a combination 10 of a light curing device 14 and a base station 12. In the case of this embodiment, a substantially stick-like light curing device 14 is likewise used, the heat absorbing element 24 extending approximately in the central region of the light curing device 14. The rear region is taken up by a handle 54, which may be in the form of a plastic sleeve 56. In the case of this solution, it is envisaged to introduce the light curing device with its heat absorbing element 24 into the base station 12 from the side, the base station having a correspondingly formed slit and, given a circular cross section of the light curing device, surrounding the heat absorbing element 24 here in a semicircular manner in the region of the recess 16, which is of a slit-like form here, and lying in good heat conducting contact there.

It is self-evident that, for example, a rectangular form, at least of the heat absorbing element 24, can also be realized in the case of this embodiment, then making it possible for the heat absorbing element 24 to lie against the base station 12 on three sides of its circumference, that is to say for example over 75% of its circumference.

Figure 9:
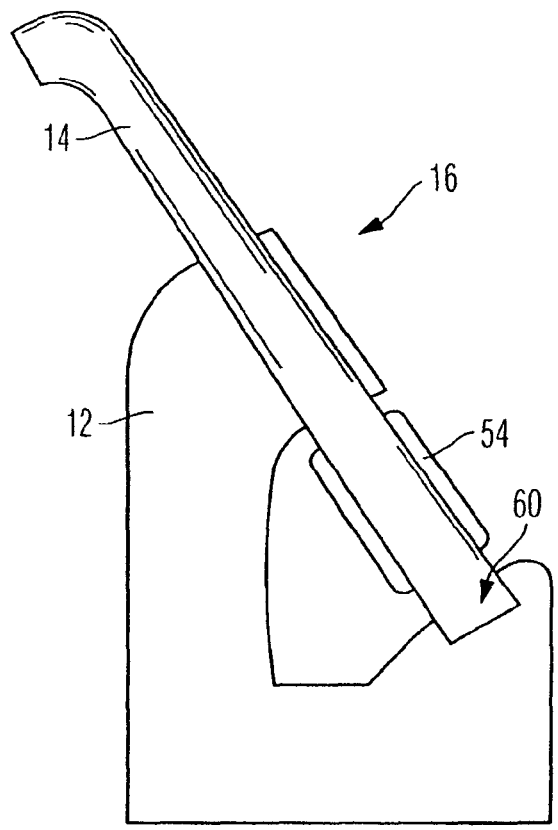
FIG. 9 shows a further embodiment of a light curing device according to the invention together with a base station.

A further embodiment of the light curing device according to the invention can be seen from FIG. 9. In the case of this embodiment, the base station 12 is formed in such a way that it forms a slightly obliquely inclined receiving region 16. The rearmost region of the light curing device 16 car be supported by means of a plug-in receptacle 60. This embodiment is likewise intended for a stick-like light curing device 14. Alternatively, this embodiment can be combined with a pistol-like light curing device, a receptacle for the handle then being provided instead of the plug-in receptacle 60, the heat absorbing element 24 at the same time being insertable into the recess 16.

Figure 10:
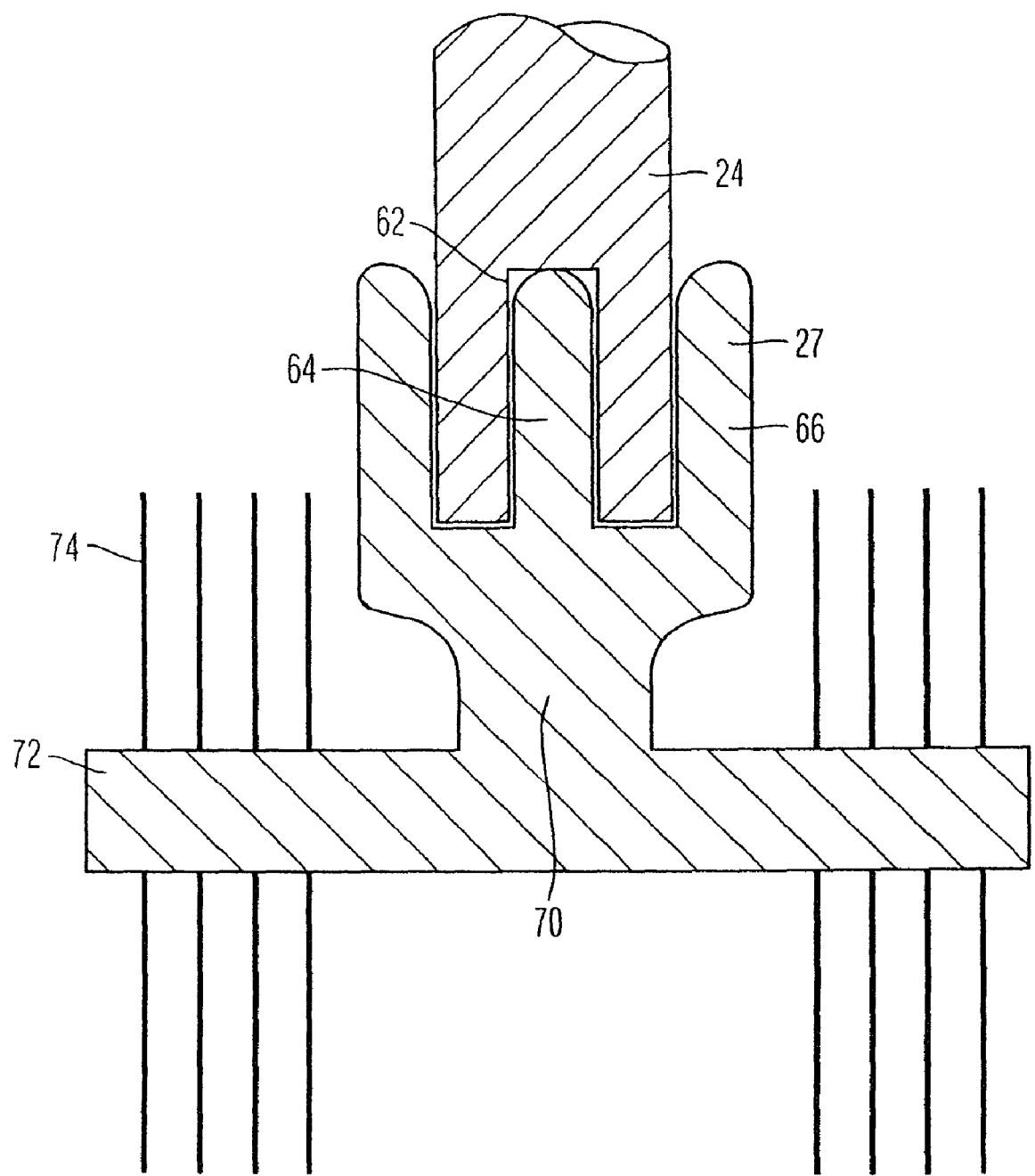
FIG. 10 shows a detailed view of a further embodiment of a light curing device/base station combination according to the invention.

It can be seen from FIG. 10 in what way an intensive contact can be realized between the heat absorbing element 24 and the heat dissipating device 27. In the case of this embodiment, there is in principle no appreciable heat store 20, the thermal capacitance of the metallic elements always serving in principle as a heat store.

In the case of this embodiment, the rear end of the light curing device has a bore 62. A pin 64, which together with a sleeve 66 forms the heat absorbing element 27, fits into the bore. In the case of this embodiment, the heat dissipating device 27 is connected by means of a heat pipe 70 to a heat sink 72, which has numerous cooling ribs 74, which with preference extend substantially vertically, as is known per-Se.

As can been seen from the drawings, a plastic housing (30) surrounds the light source (38), the light guide (36), and at least a portion of the heat conductor (40), the plastic housing serving as a handle. A portion of the heat conductor (40) spaced furthest away from the light source (38) is of the same diameter as the plastic housing. The portion of the heat conductor (40) spaced furthest away from the light source is provided with a cavity which receives the heat absorbing element (24), said portion acting as a metallic outer surface in the nature of a heat exchange element (25).

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A separable two component light curing device and base station assembly, wherein the light curing device is used away from the base station, and after use of the light curing device it is inserted into the base station, the base station being used for cooling the light curing device after use away from the base station, the assembly comprising:
   a stick-like light curing device including
      a heat source in the form of a light source (38),
      a light guide (36) extending away from the heat source to the front end of the stick-like light curing device,
      a heat conductor (40) on which the heat source is mounted, and
      a metallic heat absorbing element (24) in thermally conducting connection with the heat conductor (40), the heat absorbing element being located at the rear end of the stick-like light curing device; and
   a base station (12) having
      a recess (16) for receiving the metallic heat absorbing element (24) of the stick-like light curing device (14), the base station further including
      a heat dissipating device (27) including a heat store (20) adjacent the recess and which lies against the heat absorbing element (24) in a good heat transfer fit when the heat absorbing element (24) of the light curing device (14) is accommodated in the base station (12) after use, the thermal capacitance of the heat store (20) being at least twice to 5 times the thermal capacitance of the heat absorbing element (24).

2. The separable two component light curing device and base station as claimed in claim 1, wherein the heat absorbing element (24) is provided with a metallic outer surface of a beat exchange element (25) which lies against the base station (12) directly.

3. The separable two component light curing device and base station as claimed in claim 1, wherein the beat dissipating device (27) includes a cooler with a fan.

4. The separable two component light curing device and base station as claimed in claim 2, wherein the heat absorbing element and the recess (16) of the base station that is in connection with the heat store (20) have matching cross sections and wherein the metallic outer surface of the heat exchange element (25) is formed such that it is circular-symmetrical in cross section and rotatable in the recess.

5. The separable two component light curing device and base station as claimed in claim 1, wherein the rear end region of the light curing device (14) and/or the opening of the receiving region (recess 16) of the base station (12) has a flared insertion portion (26).

6. The separable two component light curing device and base station as claimed in claim 1, wherein the heat dissipating device (27) includes a fan and/or cooling ribs and wherein a cooling air stream flows through the base station (12) transversely in relation to the longitudinal extent of the light curing device that is accommodated in the base station (12).

7. The separable two component light curing device and base station as claimed in claim 1, wherein the base station (12) has a cooling element in the form of a Peltier element (32), which is in thermally conducting connection with the light curing device (14) when it is accommodated in the base station (12).

8. The separable two component light curing device and base station as claimed in claim 1, wherein the light curing device (14) bears a sliding sleeve, which covers the heat absorbing element at the rear end region of the light curing device (14) in a spring-loaded manner when the light curing device (14) is not inserted in the base station (12).

9. The separable two component light curing device and base station as claimed in claim 1, wherein the light curing device (14) is held in the base station (12) by magnetic force.

10. The separable two component light curing device and base station as claimed in claim 1, wherein there is a highly heat-conducting gel in the recess (16) of the base station (12).

11. The separable two component light curing device and base station as claimed in claim 1, wherein at least part of the heat dissipating device in the base station (12) is formed by a heat pipe.

12. The separable two component light curing device and base station as claimed in claim 1, wherein a plastic housing (30) surrounds the light source (38), the light guide (36), and at least a portion of the heat conductor (40), the plastic housing serving as a handle.

13. The separable two component light curing device and base station as claimed in claim 12 wherein a portion of the heat conductor (40) spaced furthest away from the light source (38) is of the same diameter as the plastic housing.

14. The separable two component light curing device and base station as claimed in claim 13 wherein said portion of the heat conductor (40) spaced furthest away from the light source is provided with a cavity which receives the metallic heat absorbing element (24), said portion acting as a heat exchange element (25) having a metallic outer surface.

* * * * *